(12) United States Patent
Burr

(10) Patent No.: US 12,186,567 B2
(45) Date of Patent: Jan. 7, 2025

(54) VENTRICULAR BLANKING PERIOD AFTER ATRIALLY SENSED BEATS

(71) Applicant: Cardiac Pacemakers, Inc., St. Paul, MN (US)

(72) Inventor: Jessica Burr, Boston, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 449 days.

(21) Appl. No.: 17/541,075

(22) Filed: Dec. 2, 2021

(65) Prior Publication Data

US 2022/0168566 A1 Jun. 2, 2022

Related U.S. Application Data

(60) Provisional application No. 63/120,607, filed on Dec. 2, 2020.

(51) Int. Cl.
*A61N 1/36* (2006.01)
*A61N 1/365* (2006.01)
*A61N 1/368* (2006.01)

(52) U.S. Cl.
CPC ......... *A61N 1/365* (2013.01); *A61N 1/36842* (2017.08)

(58) Field of Classification Search
CPC .. A61N 1/365; A61N 1/36842; A61N 1/3684; A61B 5/308; A61B 5/352; A61B 5/353; A61B 5/686; A61B 5/4848
See application file for complete search history.

(56) References Cited

U.S. PATENT DOCUMENTS

| | | | |
|---|---|---|---|
| 4,548,203 A | 10/1985 | Tacker, Jr. et al. |
| 4,559,946 A | 12/1985 | Mower |
| 4,637,397 A | 1/1987 | Jones et al. |
| 4,641,656 A | 2/1987 | Smits |
| 4,693,253 A | 9/1987 | Adams |
| 4,708,145 A | 11/1987 | Tacker, Jr. et al. |
| 4,763,646 A | 8/1988 | Lekholm |
| 4,774,952 A | 10/1988 | Smits |
| 4,775,950 A | 10/1988 | Terada et al. |
| 4,787,389 A | 11/1988 | Tarjan |
| 4,788,980 A | 12/1988 | Mann et al. |
| 4,800,883 A | 1/1989 | Winstrom |

(Continued)

FOREIGN PATENT DOCUMENTS

| CN | 107405492 A | 11/2017 |
|---|---|---|
| CN | 107847747 A | 3/2018 |

(Continued)

OTHER PUBLICATIONS

U.S. Appl. No. 08/720,360 U.S. Pat. No. 5,797,967, filed Sep. 27, 1996, System and Method to Reduce Defibrillation Requirements.

(Continued)

*Primary Examiner* — Rex R Holmes
(74) *Attorney, Agent, or Firm* — Schwegman Lundberg & Woessner, P.A.

(57) ABSTRACT

Systems and methods are disclosed to determine, in response to a detected atrial sense event in a first cardiac cycle, a ventricular blanking period for the first cardiac cycle and to detect a ventricular sense event in the first cardiac cycle using the received electrical information following the determined ventricular blanking period.

20 Claims, 6 Drawing Sheets

(56) References Cited

U.S. PATENT DOCUMENTS

| | | |
|---|---|---|
| 4,821,723 A | 4/1989 | Baker, Jr. et al. |
| 4,827,932 A | 5/1989 | Ideker et al. |
| 4,834,100 A | 5/1989 | Charms |
| 4,944,300 A | 7/1990 | Saksena |
| 4,984,572 A | 1/1991 | Cohen |
| 4,996,984 A | 3/1991 | Sweeney |
| 5,007,422 A | 4/1991 | Pless et al. |
| 5,085,213 A | 2/1992 | Cohen |
| 5,111,812 A | 5/1992 | Swanson et al. |
| 5,154,485 A | 10/1992 | Fleishman |
| 5,161,528 A | 11/1992 | Sweeney |
| 5,163,428 A | 11/1992 | Pless |
| 5,178,140 A | 1/1993 | Ibrahim |
| 5,265,600 A | 11/1993 | Adams et al. |
| 5,275,621 A | 1/1994 | Mehra |
| 5,282,836 A | 2/1994 | Kreyenhagen et al. |
| 5,350,401 A | 9/1994 | Levine |
| 5,366,485 A | 11/1994 | Kroll et al. |
| 5,431,682 A | 7/1995 | Hedberg |
| 5,441,521 A | 8/1995 | Hedberg |
| 5,464,429 A | 11/1995 | Hedberg et al. |
| 5,489,293 A | 2/1996 | Pless et al. |
| 5,522,853 A | 6/1996 | Kroll |
| 5,928,271 A | 7/1999 | Hess et al. |
| 5,978,707 A | 11/1999 | Krig et al. |
| 6,067,471 A | 5/2000 | Warren |
| 6,718,206 B2 | 4/2004 | Casavant |
| 7,738,954 B1 | 6/2010 | Kroll et al. |
| 8,588,907 B2 | 11/2013 | Arcot-Krishnamurthy et al. |
| 11,071,866 B2 | 7/2021 | Casavant et al. |
| 11,458,319 B2 | 10/2022 | Casavant et al. |
| 11,918,814 B2 | 3/2024 | Casavant et al. |
| 2002/0120318 A1 | 8/2002 | Kroll et al. |
| 2006/0224193 A1 | 10/2006 | Hess |
| 2007/0055184 A1 | 3/2007 | Echt et al. |
| 2011/0264158 A1 | 10/2011 | Dong et al. |
| 2011/0307026 A1 | 12/2011 | Zhu et al. |
| 2011/0319956 A1 | 12/2011 | Zhu et al. |
| 2013/0158621 A1 | 6/2013 | Ding et al. |
| 2014/0107724 A1 | 4/2014 | Shuros et al. |
| 2014/0172035 A1 | 6/2014 | Shuros et al. |
| 2016/0213272 A1 | 7/2016 | Pujar |
| 2017/0120058 A1 | 5/2017 | Ghosh et al. |
| 2019/0126049 A1 | 5/2019 | Casavant et al. |
| 2019/0126050 A1 | 5/2019 | Shuros et al. |
| 2020/0009380 A1 | 1/2020 | Casavant et al. |
| 2021/0052895 A1* | 2/2021 | Lybarger ............... A61N 1/365 |
| 2023/0001199 A1 | 1/2023 | Casavant et al. |
| 2024/0157153 A1 | 5/2024 | Casavant et al. |

FOREIGN PATENT DOCUMENTS

| | | |
|---|---|---|
| CN | 112543662 A | 3/2021 |
| EP | 0467652 | 1/1992 |
| EP | 0588124 | 3/1994 |
| EP | 3817805 B1 | 4/2022 |
| WO | WO-9528987 A1 | 11/1995 |
| WO | WO-9528988 A1 | 11/1995 |
| WO | WO-9701373 A1 | 1/1997 |
| WO | WO-2014099595 A2 | 6/2014 |
| WO | WO-2019079454 A1 | 4/2019 |
| WO | WO-2020010001 A1 | 1/2020 |

OTHER PUBLICATIONS

U.S. Appl. No. 16/459,092, filed Jul. 1, 2019, Adjustable Sensing in a His-Bundle Pacemaker.

"U.S. Appl. No. 16/459,092, Examiner Interview Summary mailed May 10, 2021", 2 pgs.

"U.S. Appl. No. 16/459,092, Non Final Office Action mailed Feb. 18, 2021", 16 pgs.

"U.S. Appl. No. 16/459,092, Non Final Office Action mailed Jul. 27, 2021", 16 pgs.

"U.S. Appl. No. 16/459,092, Response filed May 17, 2021 to Non Final Office Action mailed Feb. 18, 2021", 10 pgs.

"U.S. Appl. No. 16/459,092, Response filed Oct. 27, 2021 to Non Final Office Action mailed Jul. 27, 2021", 10 pgs.

"International Application Serial No. PCT/US2019/040144, International Preliminary Report on Patentability mailed Jan. 21, 2021", 7 pgs.

"International Application Serial No. PCT/US2019/040144, International Search Report mailed Sep. 26, 2019", 5 pgs.

"International Application Serial No. PCT/US2019/040144, Written Opinion mailed Sep. 26, 2019", 5 pgs.

Allessie, M, et al., "Regional Control of Atrial Fibrillation by Rapid Pacing in Conscious Dogs", Circulation, 84(4), (Oct. 1991), 1689-1697.

Ayers, Gregory M., et al., "Ventricular Proarrhythmic Effects of Ventricular Cycle Length and Shock Strength in a Sheep Model of Transvenous Atrial Defibrillation", Circulation, 89 (1), (Jan. 1994), 413-422.

Burri, Haran, et al., "Device Programming for His Bundle Pacing", Circulation: Arrhythmia and Electrophysiologyvol. 12, Issue 2, Feb. 2019 https://doi.org/10.1161/CIRCEP.118.006816, 11 pgs.

Dillon, S M., "Synchronized Repolarization After Defibrillation Shocks", Circulation, 85(5), (May 1992), 1865-1878.

Frazier, D W., et al., "Stimulus-Induced Critical Point-Mechanism for Electrical Initiation of Reentry in Normal Canine Myocardium", Journal of Clinical Investigation, 83, (Mar. 1989), 1039-1052.

Kenknight, B H., et al., "Regional Capture of Fibrillating Ventricular Myocardium", Circulation Research, 77(4), (Oct. 1995), 849-855.

Tang, A S., et al., "Three-Dimensional Potential Gradient Fields Generated by Intracardiac Catheter and Cutaneous Patch Electrodes", Circulation, 85 (5), (May 1992), 1857-1864.

Wharton, J M., et al., "Cardiac Potential and Potential Gradient Fields Generated by Single, Combined, and Sequential Shocks During Ventricular Defibrillation", Circulation, 85 (4), (Apr. 1992), pp. 1510-1523.

"U.S. Appl. No. 16/459,092, Final Office Action mailed Feb. 1, 2022", 18 pgs.

"U.S. Appl. No. 16/459,092, Notice of Allowance mailed May 31, 2022", 9 pgs.

"U.S. Appl. No. 16/459,092, Response filed Mar. 31, 2022 to Final Office Action mailed Feb. 1, 2022", 10 pgs.

"U.S. Appl. No. 17/940,886, Non Final Office Action mailed Mar. 31, 2023", 20 pgs.

"U.S. Appl. No. 17/940,886, Notice of Allowance mailed Oct. 25, 2023", 10 pgs.

"U.S. Appl. No. 17/940,886, Response filed Jun. 28, 2023 to Non Final Office Action mailed Mar. 31, 2023", 12 pgs.

"Chinese Application Serial No. 201980045473.4, Office Action mailed Jan. 23, 2024", w/o English Translation, 9 pgs.

"Chinese Application Serial No. 201980045473.4, Response filed May 21, 2024 to Office Action mailed Jan. 23, 2024", w/ current English claims, 15 pgs.

Dhingra, R C, et al., "Significance of the HV interval in 517 patients with chronic bifascicular block", Circulation. 64(6), (1981), 1265-71.

Habel, N., et al., "Atrial Oversensing and Optimizing His Bundle Lead Position", In: Natale A., Wang P., Al-Ahmad A., Estes N. (eds) Cardiac Electrophysiology. Springer, Cham., (2020), 569-571.

\* cited by examiner

VENTRICULAR BLANKING PERIOD AFTER ATRIALLY SENSED BEATS

CLAIM OF PRIORITY

This application claims the benefit of priority under 35 U.S.C. § 119(e) of U.S. Provisional Patent Application Ser. No. 63/120,607, filed on Dec. 2, 2020, which is herein incorporated by reference in its entirety.

TECHNICAL FIELD

This document relates generally to cardiac pacing, and more particularly, but not by way of limitation, to a ventricular blanking period after atrial sensed beats.

BACKGROUND

The heart an electro-mechanical system performing two major pumping functions at the center of the circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles).

In a normal heart, the sinoatrial (SA) node, the heart's natural pacemaker, generates electrical pulses, called action potentials, which propagate through natural electrical conduction pathways to various regions of the heart to excite the myocardial tissue of the heart. Action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction or deteriorated myocardium can cause dyssynchronous contraction of the heart, resulting in poor hemodynamic performance, including a diminished blood supply to the heart and the rest of the body.

Artificial cardiac pacing systems have developed to rectify cardiac dyssynchrony and improve hemodynamic performance. Cardiac rhythm management (CRM) devices adapted for His bundle pacing can provide electrical stimulations to one or more portions of the heart to improve heart function. Pacing via electrodes implanted in the apex of the RV are used in both single ventricular and biventricular (BiV) pacing. RV apex pacing directly excites the ventricular myocardium, rather than propagating the action potentials through the natural conduction pathways. In some patients, long-term RV apex pacing may result in loss of synchronous mechanical contraction of RV and LV, partially due to the interventricular delay in impulse propagation to the left ventricle. Permanent changes in myocardial perfusion and structure may develop over time, which may further decrease cardiac output and deteriorate ventricular function.

BiV pacing typically involves RV pacing via one lead and LV pacing via another, and can improve or restore substantially simultaneous contraction of both ventricles. However, the potential adverse impact on ventricular function produced by the RV apex pacing may still exist in bi-ventricular pacing. Additionally, compared to cardiac depolarization through AV node activation and propagation through the natural conduction pathways, BiV pacing may not produce similarly coordinated cardiac contractions. Moreover, the surgical procedure for placing the LV lead through the coronary sinus and into a vein on the left ventricular wall can be complex and challenging.

Hemodynamic response to artificial pacing can depend on many factors, including pacing site and the manner of which the pacing is performed. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional pacing because the propagation of the activation sequence can be much slower when it occurs through working myocardium versus activation through the intrinsic specialized conduction system of the heart. The cells of the specialized conduction system can propagate an activation signal about four times faster than working myocardium. His bundle pacing is an alternative to conventional ventricular pacing. Pacing the His bundle utilizes the natural conduction system, including the left and right bundle branches and Purkinje fibers, and produce efficient and coordinated cardiac response, reducing potentially long-term harmful hemodynamic effects of RV apex pacing and potentially mitigating existing bundle branch block, such as disclosed in the commonly assigned Casavant et al. U.S. application Ser. No. 16/174,816, titled "Systems and Methods for His-Bundle Pacing," herein incorporated by reference in its entirety, including its disclosure of various His bundle pacing systems, methods, and parameters.

However, His bundle pacing provides unique challenges, including difficult implant, lead configuration, and device programming challenges, such as due to the proximity of the His bundle to the atrium. Ineffective artificial cardiac pacing targeting the natural specialized cardiac conduction system may result in a complex or less efficient or effective myocardial contraction.

SUMMARY

Systems and methods are disclosed to determine, in response to a detected atrial sense event in a first cardiac cycle, a ventricular blanking period for the first cardiac cycle and to detect a ventricular sense event in the first cardiac cycle using the received electrical information following the determined ventricular blanking period.

An example (e.g., "Example 1") of subject matter (e.g., an implantable medical device) may comprise a signal receiver circuit comprising a first channel configured to receive electrical information from an atrium of a heart of a patient for a first cardiac cycle and a second channel configured to receive electrical information from a His bundle location of a ventricle of the heart of the patient for the first cardiac cycle, and an assessment circuit configured to detect an atrial sense event in the first cardiac cycle using the received electrical information from the first channel, determine, in response to the detected atrial sense event in the first cardiac cycle, a ventricular blanking period for the first cardiac cycle, and detect a ventricular sense event in the first cardiac cycle using the received electrical information from the second channel following the determined ventricular blanking period.

In Example 2, the subject matter of Example 1 may optionally be configured such that the assessment circuit is configured to detect, in response to the detected atrial sense event in the first cardiac cycle, the ventricular sense event in the first cardiac cycle following the detected atrial sense event and the determined ventricular blanking period.

In Example 3, the subject matter of any one or more of Examples 1-2 may optionally be configured to include a therapy circuit configured to generate a His bundle pacing pulse for delivery at or near a His bundle of the heart, and the assessment circuit of any one or more of Examples 1-2 may optionally be configured to control delivery of the His bundle pacing pulse, including to initiate delivery of the His bundle pacing pulse in the first cardiac cycle after the detected atrial sense event by a timing parameter.

In Example 4, the subject matter of any one or more of Examples 1-3 may optionally be configured such that assessment circuit is configured to initiate delivery of the His bundle pacing pulse using the second channel.

In Example 5, the subject matter of any one or more of Examples 1-4 may optionally be configured such that the atrium comprises the right atrium and the ventricle comprises the right ventricle and the timing parameter comprises an atrio-to-His bundle (AH) timing parameter.

In Example 6, the subject matter of any one or more of Examples 1-5 may optionally be configured such that the first channel comprises an atrial lead port, the second channel comprises a ventricular lead port, the assessment circuit is configured to determine the ventricular blanking period after a detected atrial sensed event while the implantable medical device is in a His bundle pacing mode to improve detection of ventricular events from the ventricular lead port, and the assessment circuit is configured to apply the determined ventricular blanking period to the second channel for the first cardiac cycle after the detected atrial sense event to avoid sensing a P-wave from the His bundle location of a right ventricle of the heart.

In Example 7, the subject matter of any one or more of Examples 1-6 may optionally be configured such that the ventricular blanking period is a selectable time period, between 45 and 105 ms, after a detected atrial sense event.

In Example 8, the subject matter of any one or more of Examples 1-7 may optionally be configured such that the assessment circuit is configured to detect the ventricular sense event in the first cardiac cycle after the detected atrial sense event and the determined ventricular blanking period to avoid sensing a P-wave from the His bundle location of a right ventricle of the heart.

An example (e.g., "Example 9") of subject matter (e.g., a method) may comprise receiving electrical information from an atrium of a heart of a patient for a first cardiac cycle using a first channel of a signal receiver circuit, receiving electrical information from a His bundle location of a ventricle of the heart of the patient for the first cardiac cycle using a second channel of the signal receiver circuit, detecting, using an assessment circuit, an atrial sense event in the first cardiac cycle using the received electrical information from the first channel, determining, using the assessment circuit, in response to the detected atrial sense event in the first cardiac cycle, a ventricular blanking period for the first cardiac cycle, and detecting, using the assessment circuit, a ventricular sense event in the first cardiac cycle using the received electrical information from the second channel following the determined ventricular blanking period.

In Example 10, the subject matter of Example 9 may optionally be configured such that the detecting the ventricular sense event comprises detecting, in response to the detected atrial sense event in the first cardiac cycle, the ventricular sense event in the first cardiac cycle following the detected atrial sense event and the determined ventricular blanking period.

In Example 11, the subject matter of any one or more of Examples 1-10 may optionally be configured to include generating, using a therapy circuit, a His bundle pacing pulse for delivery at or near a His bundle of the heart and controlling, using the assessment circuit, delivery of the His bundle pacing pulse, including initiating delivery of the His bundle pacing pulse in the first cardiac cycle after the detected atrial sense event by a timing parameter.

In Example 12, the subject matter of any one or more of Examples 1-11 may optionally be configured such that the atrium comprises the right atrium and the ventricle comprises the right ventricle and the timing parameter comprises an atrio-to-His bundle (AH) timing parameter.

In Example 13, the subject matter of any one or more of Examples 1-12 may optionally be configured such that the first channel comprises an atrial lead port and the second channel comprises a ventricular lead port, and such that the determining the ventricular blanking period of any one or more of Examples 1-12 includes determining the ventricular blanking period after a detected atrial sensed event while the assessment circuit is in a His bundle pacing mode to improve detection of ventricular events from the ventricular lead port.

In Example 14, the subject matter of any one or more of Examples 1-13 may optionally be configured such that the ventricular blanking period is a selectable time period, between 45 and 105 ms, after a detected atrial sense event.

In Example 15, the subject matter of any one or more of Examples 1-14 may optionally be configured such that detecting the ventricular sense event in the first cardiac cycle comprises detecting the ventricular sense event in the first cardiac cycle after the detected atrial sense event and the determined ventricular blanking period to avoid sensing a P-wave from the His bundle location of a right ventricle of the heart.

An example (e.g., "Example 16") of subject matter (e.g., an implantable medical device) may comprise a signal receiver circuit comprising a signal receiver circuit comprising a first channel configured to receive electrical information from an atrium of a heart of a patient for a first cardiac cycle and a second channel configured to receive electrical information from a His bundle location of a ventricle of the heart of the patient for the first cardiac cycle, and an assessment circuit configured to detect an atrial sense event in the first cardiac cycle using the received electrical information from the first channel, apply, in response to the detected atrial sense event in the first cardiac cycle, a ventricular blanking period to the second channel for the first cardiac cycle, and detect a ventricular sense event in the first cardiac cycle using the received electrical information from the second channel following the applied ventricular blanking period.

In Example 17, the subject matter of Example 16 may optionally be configured such that the assessment circuit is configured to detect, in response to the detected atrial sense event in the first cardiac cycle, the ventricular sense event in the first cardiac cycle following the detected atrial sense event and the applied ventricular blanking period.

In Example 18, the subject matter of any one or more of Examples 1-17 may optionally be configured to include a therapy circuit configured to generate a His bundle pacing pulse for delivery at or near a His bundle of the heart and the assessment circuit of any one or more of Examples 1-17 may optionally be configured to control delivery of the His bundle pacing pulse, including to initiate delivery of the His bundle pacing pulse in the first cardiac cycle after the detected atrial sense event by a timing parameter using the second channel.

In Example 19, the subject matter of any one or more of Examples 1-18 may optionally be configured such that the first channel comprises an atrial lead port, the second channel comprises a ventricular lead port, the assessment circuit is configured to apply the ventricular blanking period after a detected atrial sensed event while the implantable medical device is in a His bundle pacing mode to improve detection of ventricular events from the ventricular lead port, and the ventricular blanking period is a selectable time period, between 45 and 105 ms, after a detected atrial sense event.

In Example 20, the subject matter of any one or more of Examples 1-19 may optionally be configured such that the assessment circuit is configured to detect the ventricular sense event in the first cardiac cycle after the detected atrial sense event and the applied ventricular blanking period to avoid sensing a P-wave from the His bundle location of a right ventricle of the heart.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
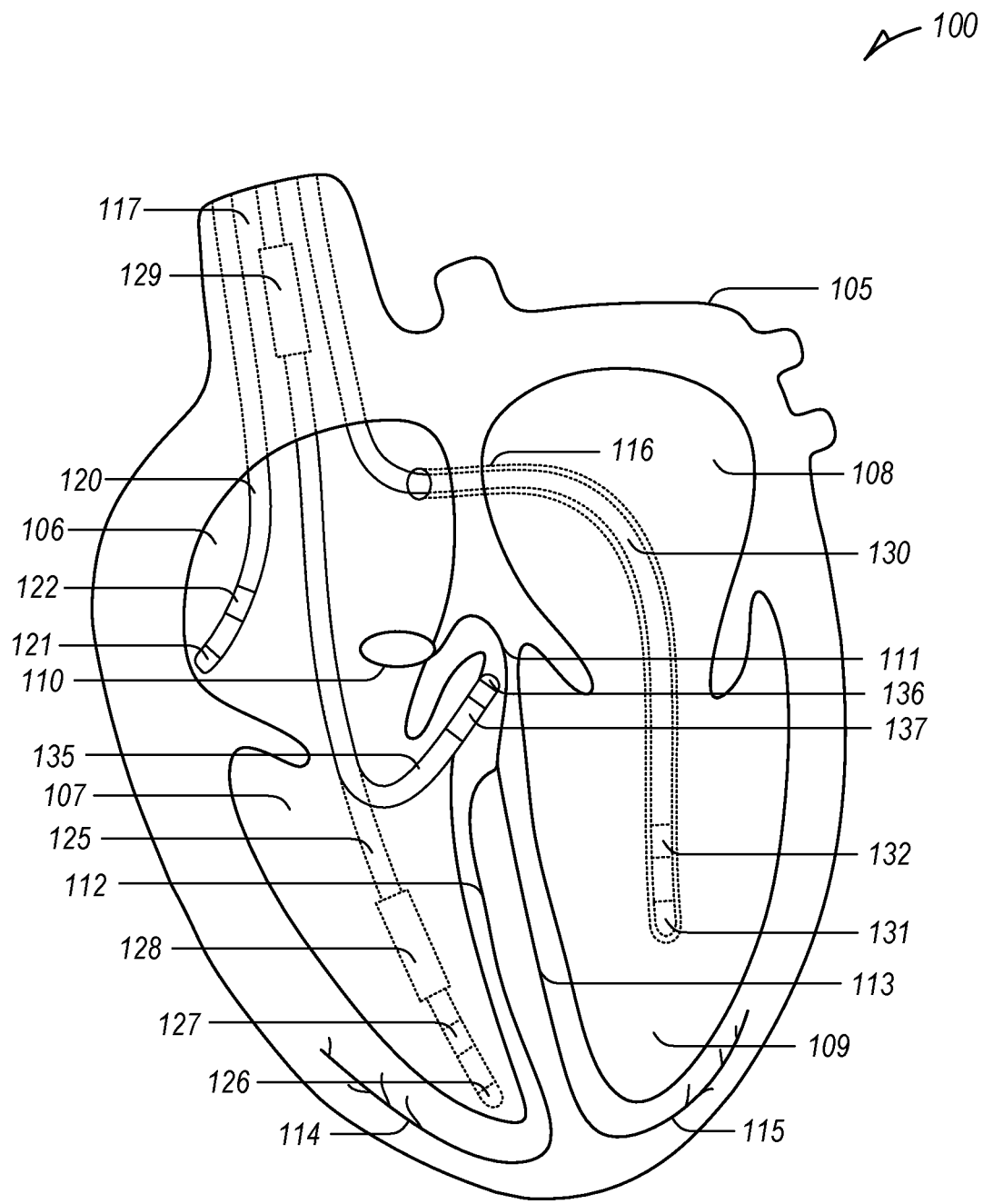
FIG. 1 illustrates example lead configurations in a heart.

Following atrial pacing, the ventricular blanking period is integral to maintaining accurate sensing from the ventricle, even more so if the lead in the ventricular port is at the His bundle. Following atrial sensing, no commensurate blanking period exists. The traditional evoked response of P-waves is generally too small to be sensed with traditional RV lead placement, and no such blanking period has developed in CRM devices adapted for His bundle pacing.

The present inventor has recognized that a ventricular blanking period after an atrial sensed event (e.g., an intrinsic atrial sensed beat) to provide a selective blanking period after the atrial sensed event during His bundle pacing can improve device operation, including improving sensing of atrial and ventricular events (e.g., intrinsic activations, responses to pacing stimulation, etc.) from the lead in the ventricular port. In an example, the ventricular blanking period after the atrial sensed event can be nominally off, so as not to affect patients without a His bundle lead, with the option to extend the ventricular blanking period after the atrial sensed event, for example, to 45 ms, 85 ms, 105 ms, etc. In other examples, the blanking period can be implemented after atrial sensed beats if the device is in a His bundle pacing mode, e.g., nominally set to 45 ms, but selectively extendable to 85 ms, 105 ms, etc., such as by a clinician, etc.

With the additional ventricular blanking period after the atrial sensed event, implantable devices can be programmed to ignore the atrial signal at the His lead and correctly sense the R-wave from the ventricle, which, without this blanking period, can be challenging. The His lead is typically placed much closer to the atrium than traditional RV lead placement. At the His bundle location in the RV, the atrial signal in the ventricle can be a similar amplitude as the ventricular signal. Adjusting sensing thresholds to avoid sensing the P-wave from the His bundle lead, but capture the R-wave, can often lead to either oversensing the P-wave or undersensing the R-wave, which can cause significant complications, including inhibition of His bundle pacing, possibly leading to asystole in pacemaker dependent patients, false declarations of tachyarrhythmia episodes, additional surgical procedures for lead revision, etc. In some examples, such complications can result in programming the His bundle device to force pace the His bundle of the patient to avoid atrial oversensing, which can result in premature battery drain.

Traditional RV pacing devices don't generally encounter these issues due to their apical or septal placement and accordingly, the option to program a blanking period after an atrial sensed event does not currently exist. The addition of a ventricular blanking period after the atrial sensed event, such as associated with His bundle pacing, can significantly decrease the complications described above, improving R-wave sensing and reducing P-wave oversensing, reducing premature battery drain, reducing unnecessary surgical intervention, and improving programming of His bundle pacing devices.

FIG. 1 illustrates example lead configurations 100 in a heart 105, including first, second, and third leads 120, 125, 130 in traditional lead placements in the right atrium (RA) 106, right ventricle (RV) 107, and in a coronary vein 116 (e.g., the coronary sinus) over the left atrium (LA) 108 and left ventricle (LV) 109, respectively, and a fourth lead 135 positioned in the RV 107 near the His bundle 111, between the AV node 110 and the right and left bundle branches 112, 113 and Purkinje fibers 114, 115. Each lead can be configured to position one or more electrodes or other sensors at various locations in or near the heart 105 to detect physiologic information or provide one or more therapies or stimulation.

The first lead 120, positioned in the RA 106, includes a first tip electrode 121 located at or near the distal end of the first lead 120 and a first ring electrode 122 located near the first tip electrode 121. The second lead 125 (dashed), positioned in the RV 107, includes a second tip electrode 126 located at or near the distal end of the second lead 125 and a second ring electrode 127 located near the second tip electrode 126. The third lead 130, positioned in the coronary vein 116 over the LV 109, includes a third tip electrode 131 located at or near the distal end of the third lead 130 and a third ring electrode 132 located near the third tip electrode 131. The fourth lead 135, positioned in the RV 107 near the His bundle 111, includes a fourth tip electrode 136 located at or near the distal end of the fourth lead 135 and a fourth ring electrode 137 located near the fourth tip electrode 136. The tip and ring electrodes can include pacing/sensing electrodes configured to sense electrical activity or provide pacing stimulation.

In addition to tip and ring electrodes, one or more leads can include one or more defibrillation coil electrodes configured to sense electrical activity or provide cardioversion or defibrillation shock energy. For example, the second lead 125 includes a first defibrillation coil electrode 128 located near the distal end of the second lead 125 in the RV 107 and a second defibrillation coil electrode 129 located a distance from the distal end of the second lead 125, such as for placement in or near the superior vena cava (SVC) 117.

Different CRM devices include different number of leads and lead placements. For examples, some CRM devices are single-lead devices having one lead (e.g., RV only, RA only, etc.). Other CRM devices are multiple-lead devices having two or more leads (e.g., RA and RV; RV and LV; RA, RV, and LV; etc.). CRM devices adapted for His bundle pacing often use lead ports designated for LV or RV leads to deliver stimulation to the His bundle 111.

However, sensing electrical activity from the RV 107 near the His bundle 111 is different than sensing electrical activity from the apex of the RV 107 or LV and invites separate challenges. In devices having the first lead 120 in the RA 106 and the fourth lead 135 in the RV 107 near the His bundle 111, atrial activity can be mistakenly sensed or determined by the fourth lead 135 as ventricular activity, potentially double counting ventricular activation. To address such issues, ventricular sensing thresholds can be raised or ventricular blanking periods can be extended to avoid oversensing atrial activity at the His bundle 111 as ventricular activity. However, raising sensing thresholds or extending existing blanking periods can lead to undersensing ventricular activity, which can be problematic in itself. Devices having a lead at the His bundle using the LV port can turn off LV sensing, for example, if traditional sensing is otherwise available at the RV apex, such as with a backup RV lead. If such RV lead is not present or available, these problems persist. Additionally, if LV sensing is turned off, clinically valuable sensing data may not be received or available.

Figure 2:
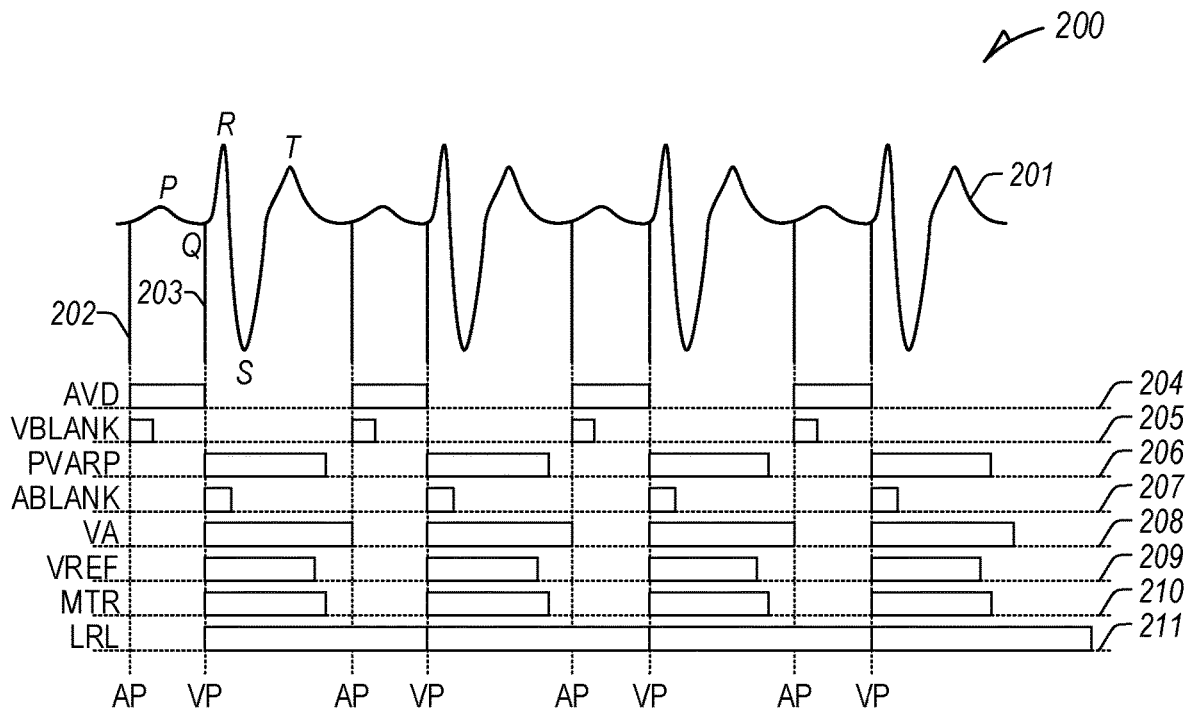
FIG. 2 illustrates example timing relationships between an example electrocardiogram (ECG) signal and associated dual-chamber timing periods.

FIG. 2 illustrates example timing relationships 200 between an example electrocardiogram (ECG) signal 201 and associated dual-chamber timing periods in response to atrial and ventricular pacing signals in a dual-chamber pacing device. The ECG signal 201 includes a P wave, a QRS complex (including Q, R, and S waves), and a T wave, and illustrates an atrial pace (AP) pulse 202 and a ventricular pace (VP) pulse 203.

The dual-chamber timing periods include an atrioventricular delay (AVD) period 204, starting with the AP pulse 202 and ending with the VP pulse 203, and a ventricular blanking (VBLANK) period 205 starting with the AP pulse 202 and ending shortly thereafter. If the AP pulse 202 is not delivered or detected, the VBLANK period 205 is not available in traditional pacing devices. The timing periods further include a post-ventricular atrial refractory period (PVARP) 206, a relative atrial refractory period that occurs after a paced or sensed ventricular event to prevent oversensing (e.g., to prevent the atrial channel from sensing the VP pulse 203, a far-field QRS complex or component thereof, or a retrograde P-wave, etc.). Similarly, the timing periods including an atrial blanking period (ABLANK) 207 after a ventricular pace, an absolute atrial refractory period shorter than the PVARP 206.

The remaining dual-chamber timing periods include the ventriculoatrial (VA) interval 208, the time at which an AP can be delivered after a ventricular event; a ventricular reference (VREF) window 209, a sensed window comprising the QRS complex and the T wave; a maximum tracking rate (MTR) 210, the fastest rate at which the device can pace following a ventricular event; and a lower rate limit (LRL) 211, the rate at which the device will pace the ventricle if no intrinsic event is detected.

Figure 3:
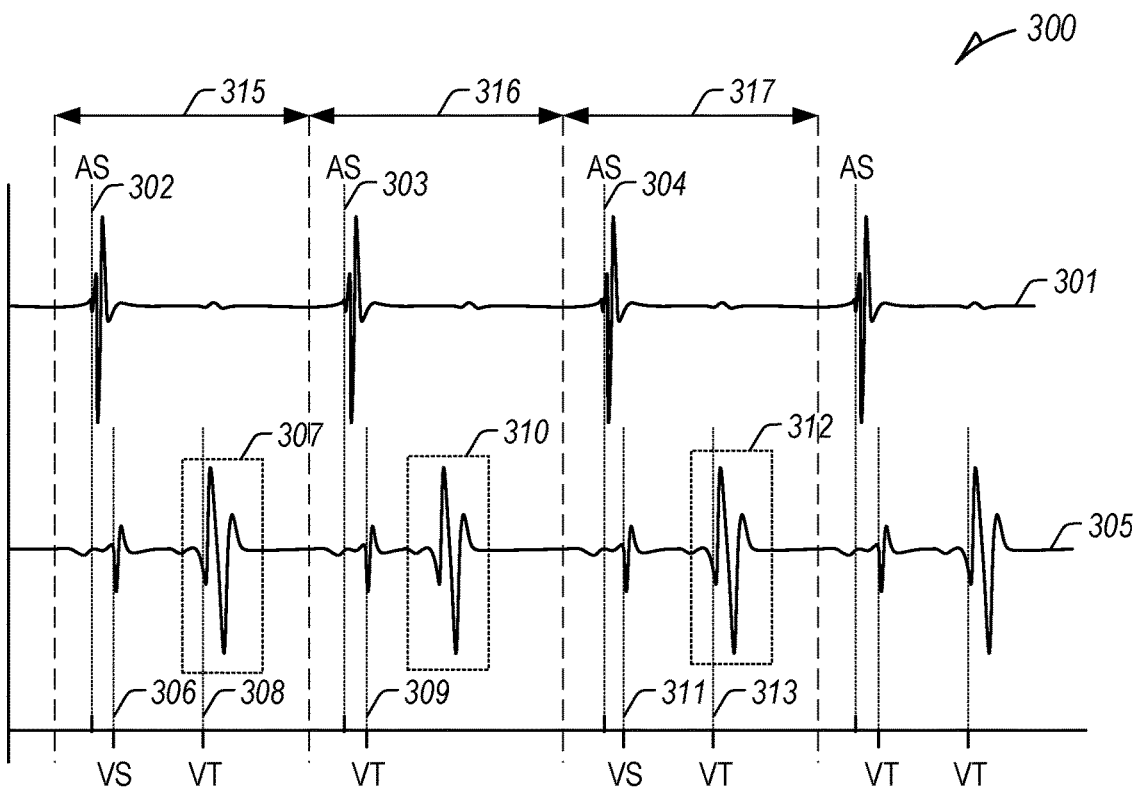
FIG. 3 illustrates example relationship between sensed events on atrial electrocardiogram (ECG) signal and a ventricular ECG signal.

FIG. 3 illustrates example relationship 300 between sensed events on atrial electrocardiogram (ECG) signal 301 detected from a lead in an atrium and a ventricular ECG signal 305 detected from a lead at a location near the His bundle in a ventricle, without a ventricular blanking period following an atrial sensed event. First, second, and third atrial sense (AS) events 302, 303, 304 are detected on the atrial ECG signal 301 in respective first, second, and third cardiac cycles 315, 316, 317. First, second, and third true ventricular sense (VS) events 307, 310, 312 are present on the ventricular ECG signal 305 in each of the first, second, and third cardiac cycles 315, 316, 317, but not detected as such.

Due to the location of the lead in the ventricle, near the His bundle, the first AS event 302 is improperly sensed as a first ventricular sense (VS) event 306 on the ventricular ECG signal 305. The first true VS event 307 is sensed as a first ventricular tachycardia (VT) event 308 on the ventricular ECG signal 305 due to the short interval (and high rate) between successive sensed ventricular events (the first VS event 306 and the first VT event 308). Similarly, the second AS event 303 is sensed as a second VT event 309 on the ventricular ECG signal 305. The second true VS event 310 falls within a post-ventricular atrial refractory period (PVARP) after the sensed second VT event 307, and is not sensed at all. The third AS event 304 is sensed as a second VS event 311, and not a VT event due to the missed second true VS event 310. With a ventricular blanking period after first, second, and third AS events 302, 303, 304 on the ventricular ECG signal 305, each of the first, second, and third true VS events 307, 310, 312, would have been properly sensed on the ventricular ECG signal 305.

Figure 4:
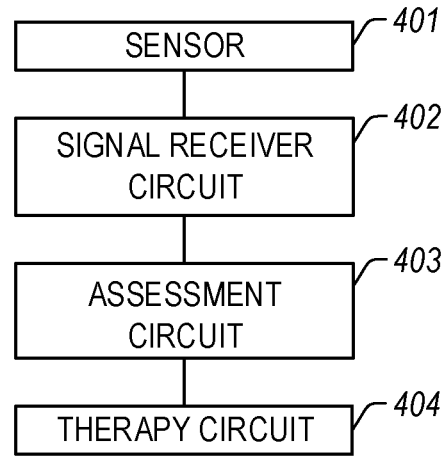
FIG. 4 illustrates an example system adapted for His bundle pacing.

FIG. 4 illustrates an example system 400 adapted for His bundle pacing, such as a medical-device system, a cardiac rhythm management (CRM) device, etc. In an example, one or more aspects of the example system 400 can be a component of, or communicatively coupled to, an ambulatory medical device (AMD), such as an implantable cardiac monitor (ICM), etc. AMDs can be configured to monitor, detect, or treat various physiologic conditions of the body, such as cardiac conditions associated with a reduced ability of a heart to sufficiently deliver blood to a body, including heart failure (HF), arrhythmias, dyssynchrony, etc., or one or more other physiologic conditions and, in certain examples, can be configured to provide electrical stimulation or one or more other therapies or treatments to the patient.

The system 400 can include a single AMD or a plurality of AMDs implanted in a patient's body or otherwise positioned on or about the patient to monitor patient physiologic information of the patient using one or more sensors, such as a sensor 401. In an example, the sensor 401 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a temperature sensor; a skin elasticity sensor, or one or more other sensors configured to receive physiologic information of the patient.

The example system 400 can include a signal receiver circuit 402 and an assessment circuit 403. The signal receiver circuit 402 can be configured to receive physiologic information of a patient (or group of patients) from one or more sensors, such as the sensor 401, etc. The assessment circuit 403 can be configured to receive information from the signal receiver circuit 402, and to determine one or more parameters (e.g., physiologic parameters, stratifiers, etc.) or existing or changed patient conditions (e.g., indications of patient dehydration, respiratory condition, cardiac condition (e.g. HF, arrhythmia), SDB, etc.) using the received physiologic information, such as described herein. The physiologic information can include, among other things, cardiac electrical information, impedance information, respiration information, heart sound information, activity information, posture information, temperature information, or one or more other types of physiologic information. In an example, the assessment circuit 403 can be configured to determine one or more timing parameters or relationships, such as one or more blanking periods, in relation to one or more leads or channels of a CRM device. In an example, the assessment circuit 403 can be configured to determine and implement, on a lead or channel configured for His bundle pacing, a ventricular blanking period following a detected atrial sense event on an atrial lead or channel, such as to avoid oversensing an atrial signal in the ventricle at the His bundle pacing location.

The assessment circuit 403 can be configured to provide an output to a user, such as to a display or one or more other user interface, the output including a score, a trend, an alert, or other indication. In other examples, the assessment circuit 403 can be configured to provide an output to another circuit, machine, or process, such as a therapy circuit 404 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 404 can include one or more of a stimulation control circuit, a cardiac stimulation circuit, a neural stimulation circuit, a dosage determination or control circuit, etc. In other examples, the therapy circuit 404 can be controlled by the assessment circuit 403, or one or more other circuits, etc.

Traditional cardiac rhythm management (CRM) devices, such as implantable cardiac monitors (ICMs), pacemakers, defibrillators, or cardiac resynchronizers, include implantable or subcutaneous devices having hermetically sealed housings configured to be implanted in a chest of a patient. The CRM device can include one or more leads to position one or more electrodes or other sensors at various locations in or near the heart, such as in one or more of the atria or ventricles, such as illustrated in FIG. 1, etc. Accordingly, CRM devices can include aspects located subcutaneously, though proximate the distal skin of the patient, as well as aspects, such as leads or electrodes, located near one or more organs of the patient. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient.

Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Figure 5:
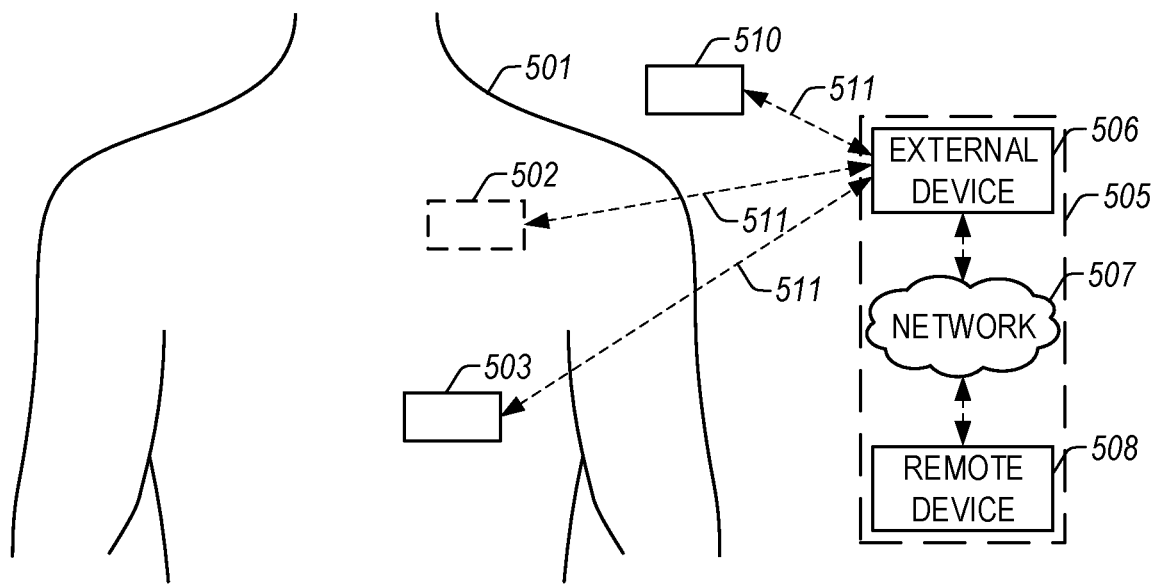
FIG. 5 illustrates an example patient management system and portions of an environment in which the system may operate.

FIG. 5 illustrates an example patient management system 500 and portions of an environment in which the system 500 may operate. The patient management system 500 can perform a range of activities, including remote patient monitoring and diagnosis of a disease condition. Such activities can be performed proximal to a patient 501, such as in a patient home or office, through a centralized server, such as in a hospital, clinic, or physician office, or through a remote workstation, such as a secure wireless mobile computing device.

The patient management system 500 can include one or more ambulatory medical devices (AMDs), an external system 505, and a communication link 511 providing for communication between the one or more AMDs and the external system 505. The one or more AMDs can include an implantable medical device (IMD) 502 (e.g., an implantable cardiac monitor (ICM), etc.), a wearable medical device 503, or one or more other implantable, leadless, subcutaneous, external, wearable, or AMDs configured to monitor, sense, or detect information from, determine physiologic information about, or provide one or more therapies to treat various conditions of the patient 501, such as one or more cardiac or non-cardiac conditions (e.g., dehydration, SDB, etc.).

In an example, the IMD 502 can include one or more traditional cardiac rhythm management (CRM) or implantable cardiac monitor (ICM) devices, such as a pacemaker or defibrillator, implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 501. In another example, the IMD 502 can include a monitor implanted, for example, subcutaneously in the chest of patient 501, the IMD 502 including a housing containing circuitry and, in certain examples, one or more sensors, such as a temperature sensor, etc.

The IMD 502 can include an assessment circuit configured to detect or determine specific physiologic information of the patient 501, or to determine one or more conditions or provide information or an alert to a user, such as the patient 501 (e.g., a patient), a clinician, or one or more other caregivers or processes. The IMD 502 can alternatively or additionally be configured as a therapeutic device configured to treat one or more medical conditions of the patient 501. The therapy can be delivered to the patient 501 via the lead system and associated electrodes or using one or more other delivery mechanisms. The therapy can include delivery of one or more drugs to the patient 501 using the IMD 502 or one or more of the other AMDs. In some examples, therapy can include CRT for rectifying dyssynchrony and improving cardiac function in CHF patients. In other examples, the IMD 502 can include a drug delivery system, such as a drug infusion pump to deliver drugs to the patient for managing arrhythmias or complications from arrhythmias, hypertension, or one or more other physiologic conditions. In other examples, the IMD 502 can include one or more electrodes configured to stimulate the nervous system of the patient or to provide stimulation to the muscles of the patient airway, etc.

The wearable medical device 503 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

The external system 505 can include a dedicated hardware/software system, such as a programmer, a remote server-based patient management system, or alternatively a system defined predominantly by software running on a standard personal computer. The external system 505 can manage the patient 501 through the IMD 502 or one or more other AMDs connected to the external system 505 via a communication link 511. In other examples, the IMD 502 can be connected to the wearable device 503, or the wearable device 503 can be connected to the external system 505, via the communication link 511. This can include, for example, programming the IMD 502 to perform one or more of acquiring physiologic data, performing at least one self-diagnostic test (such as for a device operational status), analyzing the physiologic data to detect a cardiac arrhythmia, or optionally delivering or adjusting a therapy to the patient 501. Additionally, the external system 505 can send information to, or receive information from, the IMD 502 or the wearable device 503 via the communication link 511. Examples of the information can include real-time or stored physiologic data from the patient 501, diagnostic data, such as detection of patient hydration status, hospitalizations, responses to therapies delivered to the patient 501, or device operational status of the IMD 502 or the wearable device 503 (e.g., battery status, lead impedance, etc.). The communication link 511 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 505 can include an external device 506 in proximity of the one or more AMDs, and a remote device 508 in a location relatively distant from the one or more AMDs, in communication with the external device 506 via a communication network 507. Examples of the external device 506 can include a medical device programmer.

The remote device 508 can be configured to evaluate collected patient or patient information and provide alert notifications, among other possible functions. In an example, the remote device 508 can include a centralized server acting as a central hub for collected data storage and analysis. The server can be configured as a uni-, multi-, or distributed computing and processing system. The remote device 508 can receive data from multiple patients. The data can be collected by the one or more AMDs, among other data acquisition sensors or devices associated with the patient 501. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 508 may additionally include one or more locally configured clients or remote clients securely connected over the communication network 507 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 508, including the server and the interconnected clients, may also execute a follow-up scheme by sending follow-up requests to the one or more AMDs, or by sending a message or other communication to the patient 501 (e.g., the patient), clinician or authorized third party as a compliance notification.

The communication network 507 can provide wired or wireless interconnectivity. In an example, the communication network 507 can be based on the Transmission Control Protocol/Internet Protocol (TCP/IP) network communication specification, although other types or combinations of networking implementations are possible. Similarly, other network topologies and arrangements are possible.

One or more of the external device 506 or the remote device 508 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 506 or the remote device 508 can include a respective display unit for displaying the physiologic or functional signals, or alerts, alarms, emergency calls, or other forms of warnings to signal the detection of arrhythmias. In some examples, the external system 505 can include an external data processor configured to analyze the physiologic or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 505 can be implemented using hardware, software, firmware, or combinations thereof. Portions of the one or more AMDs or the external system 505 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The therapy device 510 can be configured to send information to or receive information from one or more of the AMDs or the external system 505 using the communication link 511. In an example, the one or more AMDs, the external device 506, or the remote device 508 can be configured to control one or more parameters of the therapy device 510. The external system 505 can allow for programming the one or more AMDs and can receives information about one or more signals acquired by the one or more AMDs, such as can be received via a communication link 511. The external system 505 can include a local external IMD programmer. The external system 505 can include a remote patient management system that can monitor patient status or adjust one or more therapies such as from a remote location.

Figure 6:
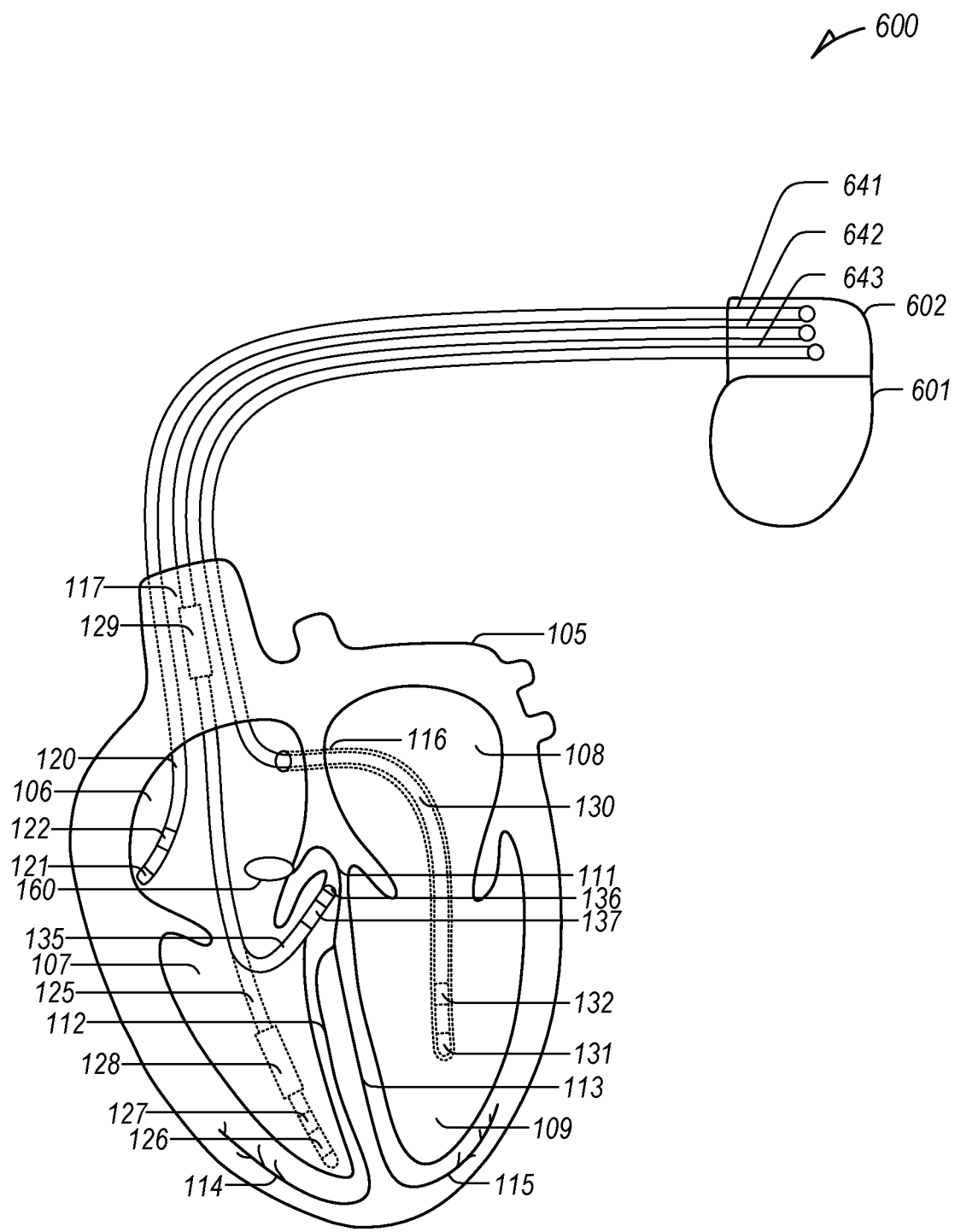
FIG. 6 illustrates an example implantable medical device (IMD) electrically coupled to a heart.

FIG. 6 illustrates an example implantable medical device (IMD) 600 electrically coupled to a heart 105, such as through one or more leads coupled to the IMD 600 through one or more lead ports, such as first, second, or third lead ports 641, 642, 643 in a header 602 of the IMD 600. In an example, the IMD 600 can include an antenna, such as in the header 602, configured to enable communication with an external system (e.g., the external system 505) and one or more electronic circuits (e.g., the assessment circuit 403) in a hermetically sealed housing (CAN) 601.

The IMD 600 may include an implantable medical device (IMD), such as an implantable cardiac monitor (ICM), pacemaker, defibrillator, cardiac resynchronizer, or other subcutaneous IMD or cardiac rhythm management (CRM) device configured to be implanted in a chest of a subject, having one or more leads to position one or more electrodes or other sensors at various locations in or near the heart 105, such as in one or more of the atria or ventricles. Separate from, or in addition to, the one or more electrodes or other sensors of the leads, the IMD 600 can include one or more electrodes or other sensors (e.g., a pressure sensor, an accelerometer, a gyroscope, a microphone, etc.) powered by a power source in the IMD 600. The one or more electrodes or other sensors of the leads, the IMD 600, or a combination thereof, can be configured detect physiologic information from, or provide one or more therapies or stimulation to, the patient.

Implantable devices can additionally include leadless cardiac pacemakers (LCP), small (e.g., smaller than traditional implantable devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart 105 without traditional lead or implantable device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

The IMD 600 can include one or more electronic circuits configured to sense one or more physiologic signals, such as an electrogram or a signal representing mechanical function of the heart 105. In certain examples, the CAN 601 may function as an electrode such as for sensing or pulse delivery. For example, an electrode from one or more of the leads may be used together with the CAN 601 such as for unipolar sensing of an electrogram or for delivering one or more pacing pulses. A defibrillation electrode (e.g., the first defibrillation coil electrode 128, the second defibrillation coil electrode 129, etc.) may be used together with the CAN 601 to deliver one or more cardioversion/defibrillation pulses.

In an example, the IMD 600 can sense impedance such as between electrodes located on one or more of the leads or the CAN 601. The IMD 600 can be configured to inject current between a pair of electrodes, sense the resultant voltage between the same or different pair of electrodes, and determine impedance, such as using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing, etc. In an example, the IMD 600 can be configured to inject current between an electrode on one or more of the first, second, third, or fourth leads 120, 125, 130, 135 and the CAN 601, and to sense the resultant voltage between the same or different electrodes and the CAN 601.

The IMD 600 can integrate one or more other physiologic sensors to sense one or more other physiologic signals, such as one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature. The arrangement and functions of these leads and electrodes are described above by way of example and not by way of limitation. Depending on the need of the patient and the capability of the implantable device, other arrangements and uses of these leads and electrodes are.

Figure 7:
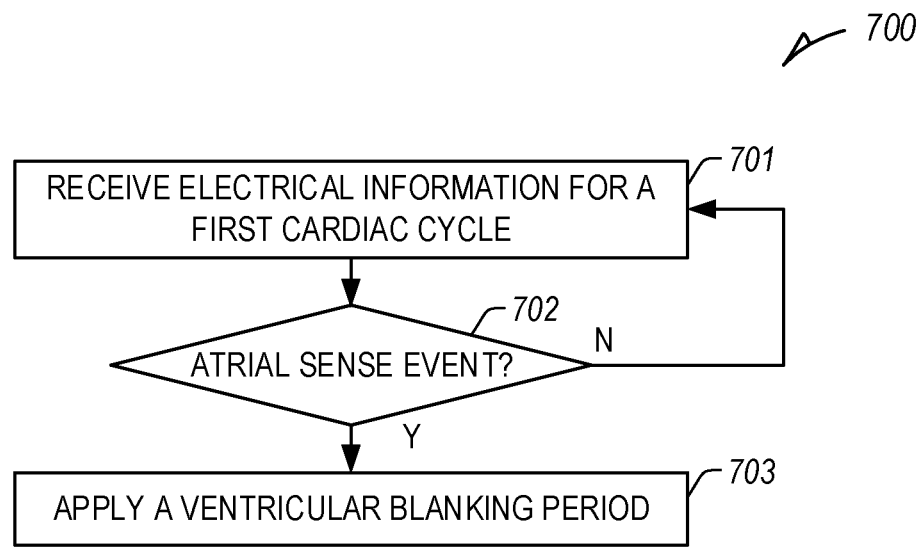
FIG. 7 illustrates an example method to determine and apply a ventricular blanking period after an atrial sense event.

FIG. 7 illustrates an example method 700 to determine and apply a ventricular blanking period after an atrial sense event. At 701, electrical information can be received for a first cardiac cycle, such as by a signal receiver circuit of an implantable medical device. A first channel of the signal receiver circuit, such as an atrial channel, can receive electrical information from an atrium of a heart of a patient. The atrial channel can include an atrial lead port configured to receive a lead configured for placement in a right atrium (RA) of the heart. A second channel of the signal receiver circuit, such as a ventricular channel, can receive electrical information from a His bundle location of a ventricle of the heart of the patient. The ventricular channel can include a ventricular lead port configured to receive a lead for placement at a His bundle location of a right ventricle (RV) of the heart.

At 702, if an atrial sense event (e.g., an atrial intrinsic activation) is detected in the first cardiac cycle using the received electrical information from the first channel, a ventricular blanking period can be applied at 703 to the electrical information from the second channel, such as using an assessment circuit. The assessment circuit can apply the ventricular blanking period, starting after the detected atrial sense event and extending for a period of time (e.g., a selectable period between 45 ms and 105 ms). The assessment circuit can detect a ventricular sense event in the first cardiac cycle using the received electrical information from the second channel after the ventricular blanking period expires, but before the start of a second cardiac cycle.

In an example, a therapy circuit can generate His bundle pacing pulses for delivery at or near the His bundle of the heart using the second channel (e.g., the ventricular channel, the ventricular lead port, etc.). The assessment circuit can control delivery of the His bundle pacing pulse, including initiating delivery of the His bundle pacing pulse a timing parameter, such as an atrio-to-His bundle (AH) timing parameter, after the detected atrial sense event. In an example, the AH timing parameter can be a set period relative to an atrial sense or an atrial pace event, or dynamic based on an intrinsic PR interval or sensed or programmed AV delay, such as 50 ms shorter than the intrinsic PR interval or the sensed or programmed AV delay, etc. In other examples, one or more of the parameters or values can be dependent on (e.g., adjustable up or down, such as by a percentage, etc.) one or more other features, such as sensed heart rate, activity, respiration, etc.

Figure 8:
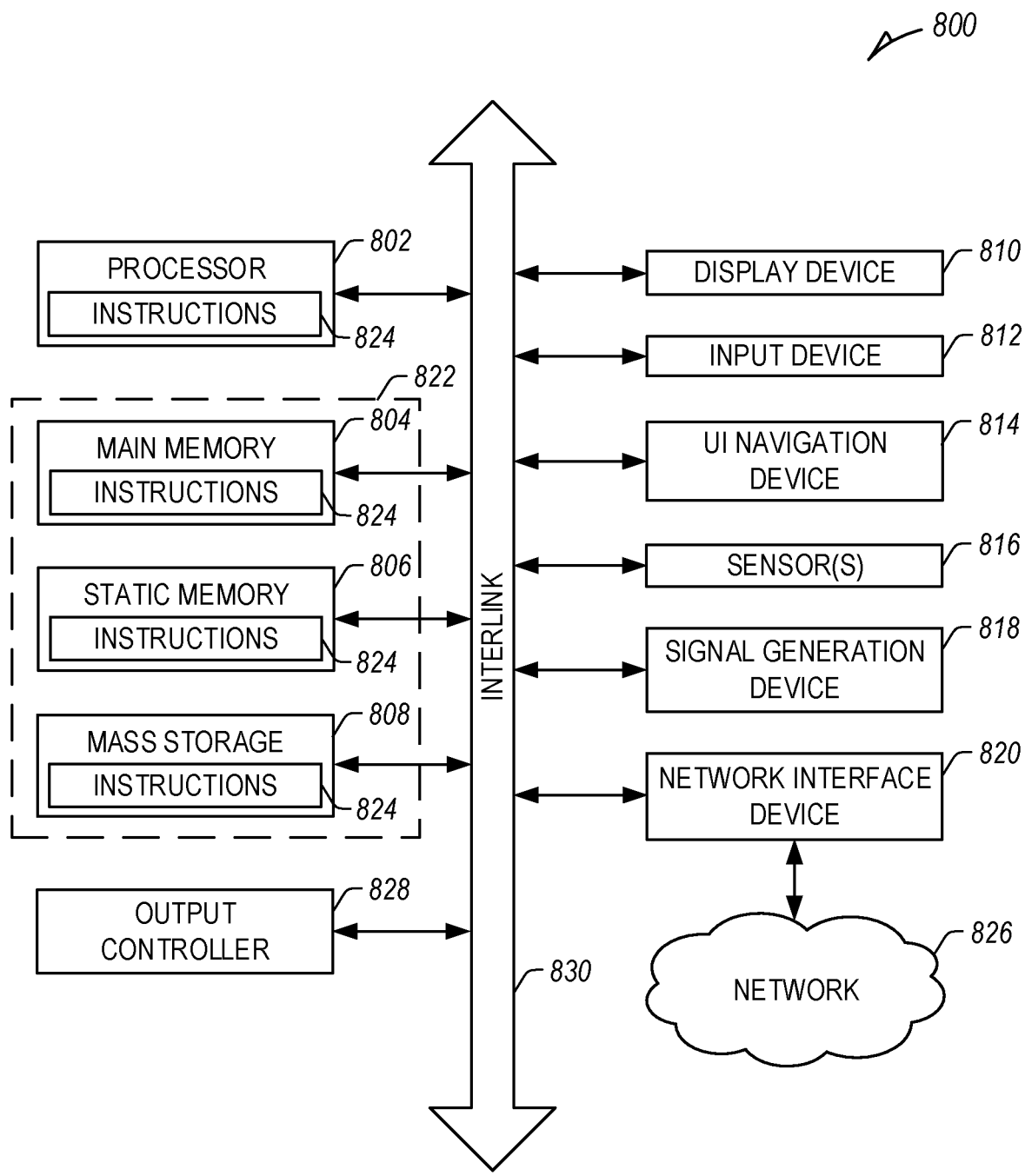
FIG. 8 illustrates a block diagram of an example machine upon which any one or more of the techniques (e.g., methodologies) discussed herein may perform.

FIG. 8 illustrates a block diagram of an example machine 800 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 800. Circuitry (e.g., processing circuitry, an assessment circuit, etc.) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812, and UI navigation device 814 may be a touch screen display. The machine 800 may additionally include a signal generation device 818 (e.g., a speaker), a network interface device 820, and one or more sensors 816, such as a global positioning system (GPS) sensor, compass, accelerometer, or one or more other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable medium 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 800, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. An implantable medical device, comprising:
a signal receiver circuit comprising:
a first channel configured to receive electrical information from an atrium of a heart of a patient for a first cardiac cycle; and
a second channel configured to receive electrical information from a His bundle location of a ventricle of the heart of the patient for the first cardiac cycle; and an assessment circuit configured to:
  detect an atrial sense event in the first cardiac cycle using the received electrical information from the first channel;
  determine, in response to the detected atrial sense event in the first cardiac cycle, a ventricular blanking period for the first cardiac cycle; and
  detect a ventricular sense event in the first cardiac cycle using the received electrical information from the second channel following the determined ventricular blanking period.

2. The implantable medical device of claim 1, wherein the assessment circuit is configured to detect, in response to the detected atrial sense event in the first cardiac cycle, the ventricular sense event in the first cardiac cycle following the detected atrial sense event and the determined ventricular blanking period.

3. The implantable medical device of claim 1, comprising:
  a therapy circuit configured to generate a His bundle pacing pulse for delivery at or near a His bundle of the heart,
  wherein the assessment circuit is configured to control delivery of the His bundle pacing pulse, including to initiate delivery of the His bundle pacing pulse in the first cardiac cycle after the detected atrial sense event by a timing parameter.

4. The implantable medical device of claim 1, wherein the first channel comprises an atrial lead port,
  wherein the second channel comprises a ventricular lead port,
  wherein the assessment circuit is configured to determine the ventricular blanking period after a detected atrial sensed event while the implantable medical device is in a His bundle pacing mode to improve detection of ventricular events from the ventricular lead port, and
  wherein the assessment circuit is configured to apply the determined ventricular blanking period to the second channel for the first cardiac cycle after the detected atrial sense event to avoid sensing a P-wave from the His bundle location of a right ventricle of the heart.

5. The implantable medical device of claim 1, wherein the ventricular blanking period is a selectable time period, between 45 and 105 ms, after a detected atrial sense event.

6. The implantable medical device of claim 1, wherein the assessment circuit is configured to detect the ventricular sense event in the first cardiac cycle after the detected atrial sense event and the determined ventricular blanking period to avoid sensing a P-wave from the His bundle location of a right ventricle of the heart.

7. A method comprising:
  receiving electrical information from an atrium of a heart of a patient for a first cardiac cycle using a first channel of a signal receiver circuit;
  receiving electrical information from a His bundle location of a ventricle of the heart of the patient for the first cardiac cycle using a second channel of the signal receiver circuit;
  detecting, using an assessment circuit, an atrial sense event in the first cardiac cycle using the received electrical information from the first channel;
  determining, using the assessment circuit, in response to the detected atrial sense event in the first cardiac cycle, a ventricular blanking period for the first cardiac cycle; and
  detecting, using the assessment circuit, a ventricular sense event in the first cardiac cycle using the received electrical information from the second channel following the determined ventricular blanking period.

8. The method of claim 7, wherein detecting the ventricular sense event comprises detecting, in response to the detected atrial sense event in the first cardiac cycle, the ventricular sense event in the first cardiac cycle following the detected atrial sense event and the determined ventricular blanking period.

9. The method of claim 7, comprising:
  generating, using a therapy circuit, a His bundle pacing pulse for delivery at or near a His bundle of the heart; and
  controlling, using the assessment circuit, delivery of the His bundle pacing pulse, including initiating delivery of the His bundle pacing pulse in the first cardiac cycle after the detected atrial sense event by a timing parameter.

10. The method of claim 7, wherein the first channel comprises an atrial lead port,
  wherein the second channel comprises a ventricular lead port, and
  wherein determining the ventricular blanking period includes determining the ventricular blanking period after a detected atrial sensed event while the assessment circuit is in a His bundle pacing mode to improve detection of ventricular events from the ventricular lead port.

11. The method of claim 7, wherein the ventricular blanking period is a selectable time period, between 45 and 105 ms, after a detected atrial sense event.

12. The method of claim 7, wherein detecting the ventricular sense event in the first cardiac cycle comprises detecting the ventricular sense event in the first cardiac cycle after the detected atrial sense event and the determined ventricular blanking period to avoid sensing a P-wave from the His bundle location of a right ventricle of the heart.

13. An implantable medical device, comprising:
  a signal receiver circuit comprising:
    a first channel configured to receive electrical information from an atrium of a heart of a patient for a first cardiac cycle; and
    a second channel configured to receive electrical information from a His bundle location of a ventricle of the heart of the patient for the first cardiac cycle; and
  an assessment circuit configured to:
    detect an atrial sense event in the first cardiac cycle using the received electrical information from the first channel;
    apply, in response to the detected atrial sense event in the first cardiac cycle, a ventricular blanking period to the second channel for the first cardiac cycle; and
    detect a ventricular sense event in the first cardiac cycle using the received electrical information from the second channel following the applied ventricular blanking period.

14. The implantable medical device of claim 1, wherein the atrial sense event is different than an atrial pace event.

15. The implantable medical device of claim 1, wherein to determine the ventricular blanking period for the first cardiac cycle comprises to determine to apply the ventricular blanking period to the second channel responsive to the detected atrial sense event in the first cardiac cycle.

16. The implantable medical device of claim 15, wherein the determination to apply the ventricular blanking period is determined using information only from the first cardiac cycle.

17. The implantable medical device of claim 15, wherein to determine to apply the ventricular blanking period to the second channel is further responsive to an indication that the implantable medical device is in a His bundle pacing mode for the first cardiac cycle.

18. The method of claim 7, wherein the atrial sense event is different than an atrial pace event.

19. The method of claim 7, wherein determining the ventricular blanking period for the first cardiac cycle comprises determining to apply the ventricular blanking period to the second channel responsive to the detected atrial sense event in the first cardiac cycle.

20. The method of claim 19, wherein determining to apply the ventricular blanking period comprises using information only from the first cardiac cycle.

\* \* \* \* \*